US006747142B1

(12) United States Patent
Polouchine

(10) Patent No.: US 6,747,142 B1
(45) Date of Patent: Jun. 8, 2004

(54) MULTIPLE METHOXYOXALAMIDO AND SUCCINIMIDO PRECURSORS FOR NUCLEOPHILIC ADDITION

(75) Inventor: Nikolai N. Polouchine, Montgomery Village, MD (US)

(73) Assignee: Fidelity Systems, Inc., Gaithersburg, MD (US)

( * ) Notice: Subject to any disclaimer, the term of this patent is extended or adjusted under 35 U.S.C. 154(b) by 0 days.

(21) Appl. No.: 09/655,316

(22) Filed: Sep. 5, 2000

(51) Int. Cl.$^7$ ........................ C07H 21/00; C07H 21/02; C07H 19/00; G01N 33/544
(52) U.S. Cl. ................... 536/25.3; 536/23.1; 536/27.1; 436/528
(58) Field of Search .............................. 536/23.1, 25.3, 536/27.1; 436/528

(56) References Cited

U.S. PATENT DOCUMENTS

| 5,112,962 A |   | 5/1992  | Letsinger et al. |
| 5,241,060 A |   | 8/1993  | Engelhardt et al. |
| 5,466,786 A |   | 11/1995 | Buhr et al. |
| 5,507,839 A | * | 4/1996  | Tanaka ........................... 8/493 |
| 5,547,835 A |   | 8/1996  | Koster |
| 5,902,879 A | * | 5/1999  | Polouchine ................. 536/23.1 |

FOREIGN PATENT DOCUMENTS

WO   WO 98/30575   *   7/1998

OTHER PUBLICATIONS

Polushin NN. Synthesis of functionally modified oligonucleotides from methoxyoxalamido precurssors. Tetrahedron Letters, vol. 37(19): 3231–3234, 1996.*
Beloglazova et al. Site–specific cleavage of yeast tRNA(phe) by derivatives of oligonucleotides bearing bisimidazolegroups. Doklady Akademi Nauk (Russian), vol. 369, No. 6, pp 827–830, 1999.*
V. Efimov, "Recent Developments in the Synthesis of Oligonucleotides, Their Analogues and Conjugates", *Nucleic Acids Symposium*, (Aug. 6–11, 1995).
N. Polushin, "Synthesis of Functionally Modified Oligonucleotides Through 2'–Methoxyoxalamide–2'–Deoxyuridine Containing Precursors", *Nucleic Acids Symposium*, (Aug. 6–11, 1995).
N. Polushin, "Synthesis of Functionally Modified Oligonucleotides from Methoxyoxalamido Precursors", *Tetrahedron Letters*, vol. 37, No. 19, pp. 3231–3234, (1996).
N. Polushin et al., "Synthesis of Oligonucleotides Containing 2'–Azido– and 2'–Amino–2'–2'–deoxyuridine Using Phosphotriester Chemistry", *Tetrahedron Letters*, vol. 37, No. 19, pp. 3227–3230, (1996).
N. Herbert et al., "Synthesis of N–Substituted Hydroxyprolinol Phosphoramidites for the Preparation of Combinatorial Libraries", *Tetrahedron Letters*, vol. 35, No. 51, pp. 9509–9512, (1994).
P. Davis et al., "Drug Leads from Combinatorial Phosphodiester Libraries", *J. Med. Chem*, vol. 38, pp. 4363–4366, (1995).
A. MacMillan et al., "Synthesis of Functionally Tethered Oligodeoxynucleotides by the Convertible Nucleoside Approach", *J. Org. Chem*, vol. 55, pp. 5931–5933, (1990).
L. Beigelman et al., "Synthesis of 2'–modified Nucleotides and their Incorporation into Hammerhead Ribozymes", *Nucleic Acids Research*, vol. 23, No. 21, pp. 4434–4442, (1995).
N. Polushin et al., "Synthesis and Characterization of Imidazoyl–Linked Synthons and 3'–Conjugated Thymidine Derivatives", *Journal of Organic Chemistry*, vol. 58, pp. 4606–4613, (1993).
R. Alul et al., "Oxalyl–CPG: A Labile Support for Synthesis of Sensitive Oligonucleotide Derivatives", *Nucleic Acids Research*, vol. 19, No. 7, pp. 1527–1532, (1991).
A. MacMillan et al., "Engineering Tethered DNA Molecules by the Convertible Nucleoside Approach", *Tetrahedron Letters*, vol. 47, No. 14/15, pp. 2603–2616, (1991).
A. Ferentz et al., "Aminolysis of 2'–Deoxyinosine Aryl Ethers: Nucleoside Model Studies for the Synthesis of Functionally Tethered Oligonucleotides", *Nucleosides & Nucleotides*, vol. 11, No. 10, pp. 1749–1763, (1992).
F. Benseler et al., "Synthesis of Suitably–protected Phosphoramidites of 2'–Fluoro–2'–Deoxyguanosine and 2-'Amino–2'–Deoxyguanosine for Incorporation into Oligoribonucleotides", *Nucleosides & Nucleotides*, vol. 11, No. 7, pp. 1333–1351, (1992).
I. Smirnov et al., "Sequencing Oligonucleotides by Exonuclease Digestion and Delayed Extraction Matrix–Assisted Laser Desorption Ionization Time–of–Flight Mass Spectrometry", *Analytical Biochemistry*, vol. 288, pp. 19–25, (1996).
J. Goodchild, "Conjugates of Oligonucleotides and Modified Oligonucleotides: A Review of Their Synthesis and Properties", *Perspectives in Bioconjugate Chemistry*, pp. 77–99, (1993).
V. Efimov et al., "New Activators for the Phosphoramidite Oligonucleotide Synthesis", *Bioorganicheskaya Khimiya*, vol. 22, No. 2, pp. 149–152, (1996).
N. Beloglazova et al., "Site–specific Cleavage of Yeast tRNA(Phe) by Derivatives of Oligonucleotides Bearing Bisimidazole Groups", *Doklady Akademii Nauk (Russia)*, vol. 369, No. 6, pp. 827–830, (1999).

* cited by examiner

*Primary Examiner*—Jeffrey Fredman
*Assistant Examiner*—Suryaprabha Chunduru
(74) *Attorney, Agent, or Firm*—Oliff & Berridge, PLC

(57) ABSTRACT

Compounds and the synthesis of compounds containing multiple precursor groups and allowing the efficient synthesis of highly functionalized oligonucleotides and oligomers are provided. Also, a branching unit that helps to further increase the density of functional groups on synthetic oligonucleotides and oligomers is provided.

37 Claims, 1 Drawing Sheet

MULTIPLE METHOXYOXALAMIDO AND SUCCINIMIDO PRECURSORS FOR NUCLEOPHILIC ADDITION

BACKGROUND OF THE INVENTION

Oligonucleotides bearing different functional groups and other functional entities have become a commonplace tool in many diagnostic and therapeutic applications. Accordingly, a large number of nucleosidic and non-nucleosidic phosphoramidite derivatives for functionalization of synthetic oligonucleotides have been reported. However, all these reagents, except for a few examples, allow introduction of only one functional moiety per phosphoramidite unit. This limitation makes synthesis of highly functionalized oligonucleotides somewhat problematic as a considerable number of incorporations may increase the overall yield of the functionalized oligonucleotide.

A precursor strategy is a system by which a single precursor is used to manufacture a variety of different products. The use of a precursor strategy is quite common in synthetic organic chemistry. As used herein, a precursor is a molecule capable of reacting with different compounds, such as modifiers, to produce a number of different products. A precursor molecule comprises a core and one or more reactive moieties. The "core" is the part of the compound that does not generally change and the part that often, but not necessarily, possesses some specific properties critical for the desired application. Thus, the core is generally untouched upon reaction with a modifier.

A "reactive moiety" is a group that reacts in a highly effective, preferably quantitative, and specific manner with a particular modifier to form a particular product or with a mixture of modifiers to form a pool of products. If a core part of a precursor contains some functionalities that are also capable of reacting with the modifier, during the reaction, these functionalities must be protected.

A precursor strategy will work successfully only if some demands are fulfilled. These demands include the following:

1. If a precursor is a complex molecule and is prepared by multi-step synthesis, the precursor reactive moiety or moieties must be stable in all conditions used during the synthesis after its introduction. However, this rule is not applicable if a reactive moiety is introduced at the very last step of the precursor synthesis.
2. It is highly desirable for the yield of the reaction between a precursor reactive moiety and a modifier to be close to quantitative. This is especially important when the precursor contains more than one reactive moiety.
3. The core part of a precursor must be stable in the conditions of transformation, that is, the conditions under which the precursor reacts with a modifier.
4. One or more modified sites, that is, parts of a product molecule that are formed after reaction between a precursor reactive moiety and a modifier, must tolerate the deprotection conditions if a deprotection step is necessary to prepare a desired product.
5. It is desirable for the transformation time to be relatively short.

Oligonucleotides bearing various functionalities have become common place tools in molecular biology and diagnostics. Goodchild, J., "Conjugates of Oligonucleotides and Modified Oligonucleotides: A Review of Their Synthesis and Properties," Perspectives in Bioconjugate Chemistry, pp. 77–99 (1993). One of the most efficient routes to the synthesis of functionally modified oligonucleotides (FMOs) is the introduction of a precursor, that is, a nucleotide monomer bearing a reactive moiety, into the oligonucleotide. At the end of solid phase synthesis, the precursor reacts with a desired linker or modifier. This strategy enables one to synthesize a wide variety of FMOs from a single parent oligonucleotide.

MacMillan, A. and Verdine, G., "Engineering Tethered DNA Molecules by the Convertible Nucleoside Approach," Tetrahedron, 47: 2603–2619 (1991), and Ferenz, A. and Verdine, G., "Aminolysis of 2'-Deoxyinosine Aryl Ethers: Nucleoside Model Studies for the Synthesis of Functionally Tethered Oligonucleotides," Nucleosides & Nucleotides, 11: 1749–1763 (1992), have elaborated a convertible nucleoside strategy to prepare functionally tethered oligonucleotides (FTOs). This convergent strategy is based on the use of O-substituted deoxyuridine and deoxyinosine as convertible nucleosides. Upon treatment with aqueous amines, precursor oligonucleotides containing convertible nucleosides undergoes a transformation giving rise to a FTO.

Buhr et al., U.S. Pat. No. 5,466,786, described the incorporation of a 2'-deoxy-2'-O-(ethoxycarbonylmethyl)-cytidine into an oligonucleotide. After solid phase synthesis and deprotection, the ester group, which is a reactive moiety, can be hydrolyzed to a carboxy group by treatment with NaOH or derivatized to an amide or substituted amide by a reaction with $NH_3$ or a primary aliphatic amine.

Hebert et al., Tetrahedron Letters, 35: 9509–9512 (1994), reported the N-acylation of a DMT-hydroxymethylpyrrolidinol precursor with a number of carboxylic acids. N-substituted DMT-hydroxymethylpyrrolidinols were further phosphitilated and used for the preparation of phosphodiester oligomer combinatorial libraries.

U.S. Pat. No. 5,902,879 to Polouchine, the entire disclosure of which is hereby incorporated by reference, discloses the addition of individual precursor moieties to nucleosides and nucleotides and compounds synthesized therefrom. U.S. patent application Ser. No. 09/655,317, filed Sep. 5, 2000, the entire disclosure of which is hereby incorporated by reference, discloses the addition of individual precursor moieties to non-nucleosides and non-nucleotides and compounds synthesized therefrom.

SUMMARY OF THE INVENTION

The present invention provides for the synthesis of compounds containing multiple precursor groups, such as methoxyoxalamido (MOX), and allowing the efficient synthesis of highly functionalized oligonucleotides and oligomers. Also, the present invention provides a branching unit that helps to further increase the density of functional groups on synthetic oligonucleotides and oligomers. The present invention also provides for compounds containing multiple precursor groups, such as methoxyoxalamido (MOX) precursor groups.

The present invention provides a compound, or a salt thereof, having the formula (I):

$$A—X_n \qquad\qquad (I)$$

wherein A represents an organic moiety, n is at least 2, each X is independently selected from the group consisting of: —NRCOCONu, —NHCOCR₂CR₂CONu, —NHCOCR=CRCONu, —NHCOSSCONu, —NRCOCOOCR₃,

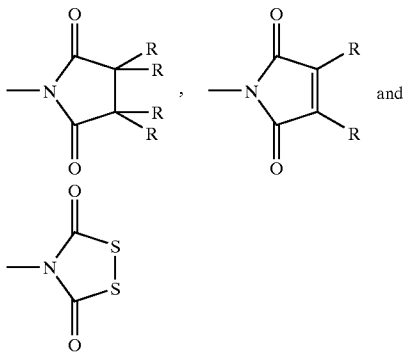

wherein each R independently represents H or a substituted or unsubstituted alkyl group, and Nu represents a nucleophile.

The present invention also provides a method for forming a compound, comprising:

reacting, by nucleophilic addition, a first compound containing a first moiety selected from the group consisting of: —NRCOCOOCR₃,

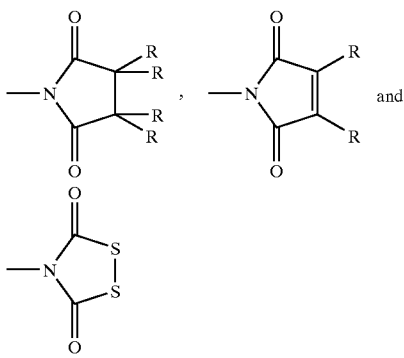

wherein each R independently represents H or a substituted or unsubstituted alkyl group, with a second compound (HNu) containing at least three primary or secondary amines to form a third compound containing a second moiety selected from the group consisting of: —NRCOCONu, —NHCOCR₂CR₂CONu, —NHCOCR=CRCONu, and —NHCOSSCONu, wherein each R independently represents H or a substituted or unsubstituted alkyl group, wherein one of the at least three primary or secondary amines of the second compound acts as a nucleophile in the nucleophilic addition, leaving at least two unreacted primary or secondary amines in the second moiety;

reacting the third compound with at least two compounds, which may be the same or different, each containing a third moiety independently selected from the group consisting of: —COCOOCR₃, —COCR₂CR₂CO—, —COCR=CRCO— and —COSSCO—, wherein each of the at least two compounds reacts with one of the at least two unreacted primary or secondary amines of the second moiety to form a compound containing at least two moieties independently selected from the group consisting of: —NRCOCOOCR₃,

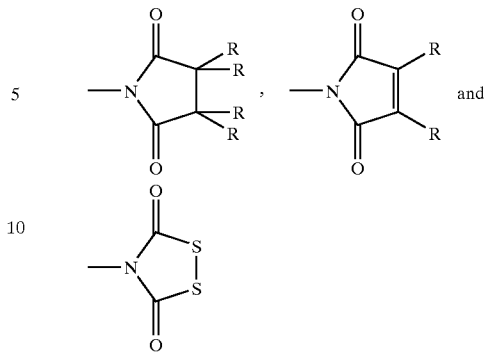

wherein each R independently represents H or a substituted or unsubstituted alkyl group.

DETAILED DESCRIPTION OF PREFERRED EMBODIMENTS

Figure 1:
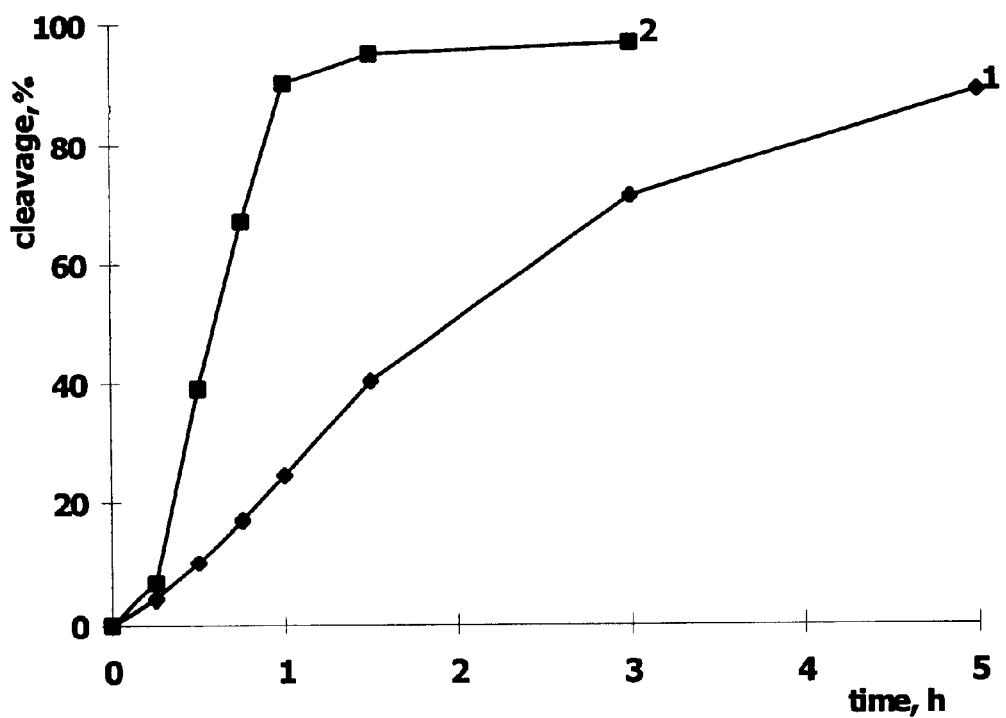
FIG. 1 shows a time course of tRNA$^{Phe}$ cleavage with oligonucleotide conjugates R2, having two imidazole groups, (curve 1) and R4, having four imidazole groups, (curve 2).

The present invention provides for compounds and the synthesis of compounds containing multiple precursor groups, such as methoxyoxalamido (MOX), providing efficient synthesis of highly functionalized oligonucleotides and oligomers. Incorporating multiple precursor groups into one monomer or compound increases the efficiency at which many reactions may be performed. Importantly, the density of functional groups may be increased by increasing the number of precursor groups on an individual compound, and/or within a defined space. In this manner, the density of the functional groups is increased. Such an increase is important for some applications where efficiency of action of a functionalized compound depends on the density and special arrangement of functional groups.

For some applications, it is desirable to control electophoretic mobility of an oligonucleotide or oligomer. One way to do so is to introduce a bulky moiety onto the 5'-end. Using multiple modifiers, such as methoxyoxalamido, it is possible to introduce several desirable moieties, thus allowing better control of electophoretic mobility. Moieties having particular desired charges may also be introduced to affect the mobility of an oligonucleotide or oligomer. Other moieties containing desired attributes, such as those bearing dyes, may also be incorporated.

The present invention provides a monomeric compound, or a salt thereof, having the formula (I):

A—X$_n$           (I)

wherein A represents an organic moiety, n is at least 2, each X is independently selected from the group consisting of: —NRCOCONu, —NHCOCR₂CR₂CONu, —NHCOCR=CRCONu, —NHCOSSCONu, —NRCOCOOCR₃,

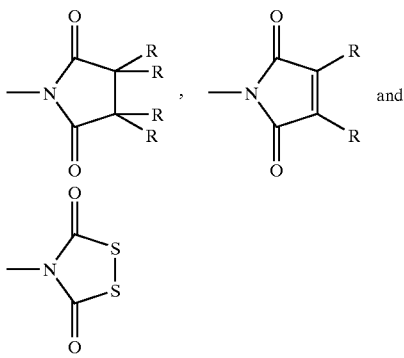

wherein each R independently represents H or a substituted or unsubstituted alkyl group, and Nu represents a nucleophile.

Nucleosides, nucleotides and modified nucleosides and nucleotides may be used as organic moieties in the present invention. Non-nucleosides or non-nucleotides may also be used as organic moieties in the present invention. Suitable non-nucleosides or non-nucleotides of the present invention include, but are not limited to, a substituted or unsubstituted alkane, such as an alkane having from 3 to 100 carbon atoms, preferably from 3 to 20 carbon atoms and more preferably from 3 to 12 carbon atoms; a substituted or unsubstituted cycloalkane, such as a cycloalkane having from 3 to 12 carbon atoms in a cycle, preferably from 4 to 8 carbon atoms in a cycle and more preferably from 5 to 6 carbon atoms in a cycle; and a substituted or unsubstituted heterocyclic compound, such as a heterocyclic compound having from 3 to 20 carbon atoms in a cycle, preferably from 3–14 carbon atoms in a cycle. The compound may be substituted with at least one substituent, such as substituents selected from the group consisting of a hydroxy group, a protected hydroxy group and a halogen.

In an embodiment of the invention, the nucleophile is selected from the group consisting of —O⁻, an amino group (—NH$_2$), a primary amino group (—NRH) and a secondary amino group (—NR$_2$). R may be a substituted or unsubstituted alkyl group. The alkyl group may preferably have from 1 to 15, more preferably from 1 to 12, and even more preferably from 1 to 6 carbon atoms.

In an embodiment of the invention, the organic moiety contains at least two hydroxy or protected hydroxy groups. In a "protected hydroxy group," the H in the hydroxy group is replaced with a "protecting group." A "protecting group" in this context is a substituent that prevents or shields the reactivity of the —OH during a reaction, but that can be removed when the reaction is completed. In particular embodiments, a protecting group prevents a reaction to link sequential nucleosides or non-nucleosides. Typical protecting groups in the compounds of the invention include 4,4'-dimethoxy trityl (DMT), 4-monomethoxytrityl and trityl.

In embodiments of the invention, the organic moiety contains at least one hydroxy or protected hydroxy group, particularly at least one hydroxy or protected hydroxy group at a secondary or tertiary carbon. In a preferred embodiment, the hydroxy or protected hydroxy group is at a secondary carbon.

In embodiments, the organic moiety contains two hydroxy or protected hydroxy groups. In a preferred embodiment, one hydroxy or protected hydroxy group is at a secondary carbon and the other hydroxy or protected hydroxy group is at a primary carbon.

In another embodiment of the invention, for example where the organic moiety will be a terminus or end unit in an oligonucleotide or oligomer, the organic moiety contains one hydroxy or protected hydroxy group.

An organic moiety may be phosphitilated at a secondary or tertiary hydroxy group, particularly to add a phosphoramidite thereto. In particular, the hydroxy group at a secondary carbon may be phosphitilated. In embodiments where there are two hydroxy groups, the other hydroxy group may be protected by a protecting group so that only one hydroxy group is phosphitilated.

Phosphitilation at a secondary or tertiary hydroxy group provides for increased stability. However, phosphitilation at a secondary hydroxy group is particularly preferred because, with phosphitilation at a tertiary hydroxy group, steric hindrance problems may be introduced that counteract the increase in stability.

Phosphoramidite compounds with a phosphoramidite group at a secondary or tertiary carbon of the organic moiety are preferable. Such an orientation increases the stability of the compound. In such compounds, degradation after storing at −20° C. may be prevented for 3–6 months, 1 year, 3 years or more. In addition, in embodiments, the phosphoramidite compounds may be in solid form. Solid phosphoramidite compounds generally show increased stability over phosphoramidite compounds in oil form.

Compounds of the present invention that contain at least one hydroxy group can undergo reactions that link the hydroxy groups. In an embodiment of the invention, phosphodiester linkages between the monomers may be formed by phosphitilation techniques known in the art.

Known phosphitilation techniques may be used to form phosphodiester linkages between the monomer and other organic moieties, which may or may not be a monomer of the present invention, such that oligonucleotides, oligomers, polynucleotides or polymers can be formed.

In a preferred embodiment of the invention, oligonucleotides or oligomers are formed using a phosphoramidite method. In a further preferred embodiment of the invention, a double mode coupling protocol is used. A double mode coupling protocol means that there are two consecutive coupling steps, with only washing in between the coupling steps. In contrast, in the standard phosphoramidite method, capping occurs between each coupling reaction.

In an embodiment of the present invention, the present invention is directed to a compound having the following formula:

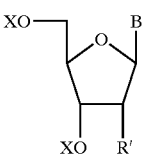

wherein each X independently represents H, a group that protects a hydroxy group, a phosphorus containing group, such as a $(PO_3)_m^{-2}$ group where m is an integer of 1–3, a group reactive to link hydroxy groups, or a phosphodiester linkage to another compound, B is a nitrogenous base, and R' contains at least two functional groups selected from the group consisting of —NRCOCONu, —NHCOCR$_2$CR$_2$CONu, —NHCOCR=CRCONu, —NHCOSSCONu, —NRCOCOOCR$_3$,

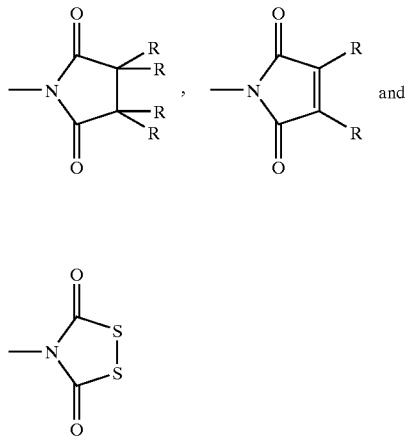

wherein each R independently represents H or a substituted or unsubstituted alkyl group, and Nu represents a nucleophile.

A "group reactive to link hydroxy groups" is an intermediate residue in the formation of a link, particularly an internucleotide link, between hydroxy groups, particularly the 5' and 3' hydroxyls. The group is typically a phosphorus containing group, such as a phosphoramidite group. The reaction of the group with a —OH of an adjacent monomer results in a linking residue, particularly a nucleotide linking residue. The linking residue may be any linking moiety conventionally used to conjugate hydroxy groups of adjacent monomers, particularly, to conjugate nucleotide residues.

The present invention is also directed to conjugate acids and salts of the compounds of the present invention. In particular, the nucleophilic groups may be bonded to a proton or a cation to form an acid or salt. For example, the present invention is directed to compounds having the following moieties: —OH, —NH$_3^+$, —NRH$_2^+$, —NR$_2$H$^+$ and —OX, where X is a cation.

Suitable reactive groups, such as methoxyoxalamido and N-succinimido moieties, can act as reactive moieties in a precursor strategy if designed as a part of a precursor molecule. In particular, they have potential as a precursor for the post synthetic introduction of various effectors onto an oligonucleotide or oligomer molecule. However, the invention is not limited to these embodiments.

In a methoxyoxalamido moiety, the ester carbonyl carbon of the methoxyoxalyl residue is highly electrophilic due to electron withdrawing effects of the adjacent methoxy and carbonyl groups. Thus, the attack of nucleophiles onto this electrophilic center occurs very quickly and efficiently. In fact, it is close to quantitative in minutes or less. This was demonstrated by reaction of 5'-dimethoxytrityl-2'-methoxyoxalamido-2'-deoxyuridine with ethanolamine, aqueous ammonia and the acetonitrile solution of 1,8-diazabicyclo[5,4,0]undec-7-ene in the presence of water (DBUH$^+$OH$^-$).

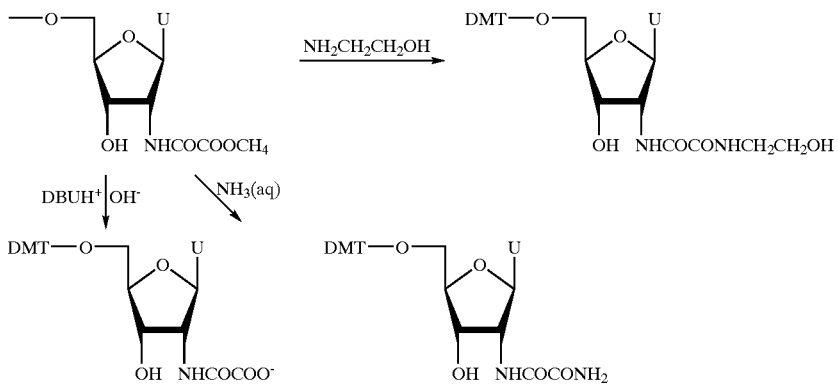

The methoxyoxalamidoalkyl moiety, if designed as part of an oligonucleotide or oligomer molecule, is a convenient site for the introduction of various functional additives. Thus, a desirable modifier, particularly if it contains an aliphatic amino group, may easily derivatize a methoxyoxalamido precursor at a methoxyoxalyl site to afford the corresponding conjugate via a stable alkylamidooxalamidoalkyl bridge (alkyl-NHCOCONH-alkyl).

In the methoxyoxalamido moiety, any of the hydrogen atoms may be substituted with an alkyl radical (NRCOCOOCR$_3$, R=alkyl). The alkyl group may be substituted or unsubstituted. Preferably, the alkyl group contains 1–12, more preferably 1–6, carbon atoms.

In a N-succinimido moiety, both carbonyl carbons of the N-succinimide moiety are equally highly electrophilic due to electron withdrawing effects of the carbonyl groups. The nucleophilic cycle opening, that is, the attack of a nucleophile onto one of the carbonyl carbons, proceeds very rapidly, usually within seconds, and in a quantitative yield. On the other hand, the amidoethyleneamido bridge (—NHCOCH$_2$CH$_2$CONH—), which is formed between the modifier and the precursor core, is stable both towards bases and acids. Thus, the product can be easily purified. Similar moieties that may be used in the described strategy include: substituted N-succinimido moieties, N-maleimido moieties, substituted N-maleimido moieties, and N-dithiasuccinimido moieties. The R groups each independently represent a substituted or unsubstituted alkyl group. Preferably, the alkyl group contains 1–12, more preferably 1–6, carbon atoms.

The present invention also provides a compound, or a salt thereof, having the formula (I):

$$A-X_n \tag{I}$$

wherein A represents an organic moiety, n is at least 2, each X is independently selected from the group consisting of: —NRCOCONu, —NHCOCR₂CR₂CONu, —NHCOCR═CRCONu, —NHCOSSCONu, —NRCOCOOCR₃,

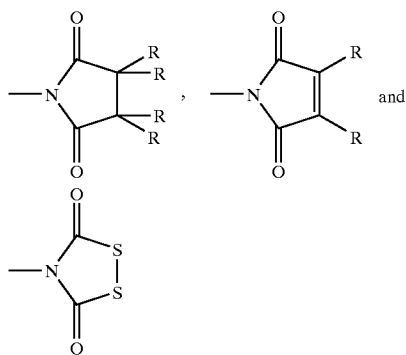

wherein each R independently represents H or a substituted or unsubstituted alkyl group, and Nu represents a nucleophile, and wherein the ratio of n to overall weight average molecular weight of the compound is from 1:100 to 1:500.

Precursor groups may be in various multiple quantities such as 2, 3, 4, 5, 6, 7, 8, 9, 10, 11, 12 or more. Precursor groups may be expressed as a ratio of number of precursor groups per overall molecular weight of the compound, such as 1 precursor group per 100 to 850 molecular weight (weight average molecular weight) of final compound, preferably 1 precursor group per 100 to 650 molecular weight of final compound, and more preferably 1 precursor group per 100 to 500 molecular weight of final compound, and even more preferably 1 precursor group per 200 to 450 molecular weight of final compound.

The present invention also provides methods for forming compounds according to the present invention, comprising:

reacting a first compound containing at least two primary or secondary amino groups with at least a second and third compound, the second compound containing a second moiety and the third compound containing a third moiety, the second and third moiety each independently selected from the group consisting of: —COCOOCR₃, —COCR₂CR₂CO—, —COCR═CRCO— and —COSSCO— to form a fourth compound containing at least a fourth and fifth moiety, each selected from the group consisting of: —NRCOCOOCR₃,

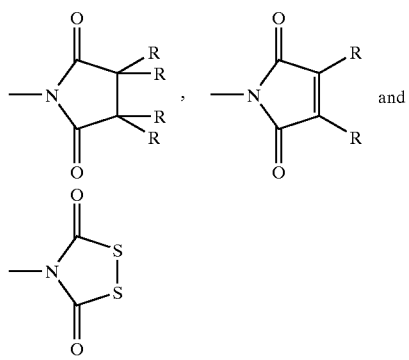

wherein each R independently represents H or a substituted or unsubstituted alkyl group.

The present invention also provides a method for forming a compound with at least two moieties, comprising:

reacting, by nucleophilic addition, a first compound containing a first moiety selected from the group consisting of: —NRCOCOOCR₃,

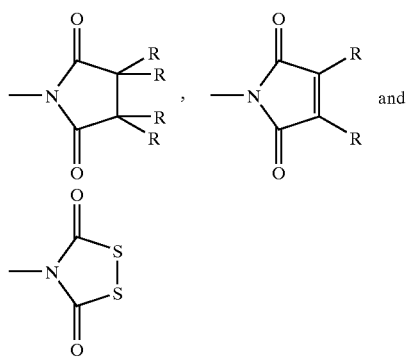

wherein each R independently represents H or a substituted or unsubstituted alkyl group, with a second compound (HNu) containing at least three primary or secondary amino groups to form a third compound containing a second moiety selected from the group consisting of: —NRCOCONu, —NHCOCR₂CR₂CONu, —NHCOCR═CRCONu, and —NHCOSSCONu, wherein each R independently represents H or a substituted or unsubstituted alkyl group, wherein one of the at least three primary or secondary amino groups of the second compound acts as a nucleophile in the nucleophilic addition, leaving at least two unreacted primary or secondary amino groups in the second moiety;

reacting the third compound with at least two compounds, which may be the same or different, each containing a third moiety independently selected from the group consisting of: —COCOOCR₃, —COCR₂CR₂CO—, —COCR═CRCO— and —COSSCO—, wherein each of the at least two compounds reacts with one of the at least two unreacted primary or secondary amino groups to form a compound containing at least two moieties independently selected from the group consisting of: —NRCOCOOCR₃,

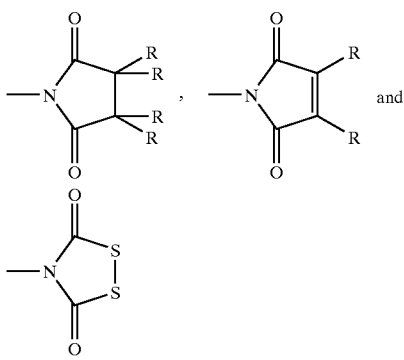

wherein each R independently represents H or a substituted or unsubstituted alkyl group.

In the various moieties, each R independently represents H or a substituted or unsubstituted alkyl group. In embodiments of the invention where the R is a substituted or unsubstituted alkyl group, the alkyl group may contain from 1 to 15, preferably from 1 to 12, and more preferably from 1 to 6 carbon atoms.

In an embodiment of the invention, the first compound is a nucleoside or nucleotide that has been modified to add the first moiety. In a preferred embodiment of the invention, the moiety is attached to a carbon atom of a ribose or deoxyribose sugar of a nucleoside or nucleotide. In a further preferred embodiment, the moiety is attached to the 2' position of a sugar.

The second compound contains at least three primary or secondary amino groups. The second compound may be any compound containing at least three amino groups as long as each amino group is susceptible to reaction with the first compound. In an embodiment of the invention, each amino group is a primary amino group. In a preferred embodiment of the invention, the carbon attached to each amino group is an aliphatic carbon. In a particular embodiment, the second compound is symmetrical. However, in other embodiments, the second compound may be unsymmetrical.

According to the method of the invention, the third compound is reacted with at least two compounds, which may be the same or different, each containing a third moiety independently selected from the group consisting of: —COCOOCR$_3$, —COCR$_2$CR$_2$CO—, —COCR=CRCO— and —COSSCO—. Thus, the third compound may be reacted with multiple compounds, each having the same moiety selected from the group consisting of: —COCOOCR$_3$,—COCR$_2$CR$_2$CO—, —COCR=CRCO— and —COSSCO—, or the third compound may be reacted with multiple compounds having different and varying combinations of such moieties. The third compound may be reacted with compounds having single or multiple moieties selected from the group consisting of: —COCOOCR$_3$,—COCR$_2$CR$_2$CO—, —COCR=CRCO— and —COSSCO—.

In the at least two compounds that are reacted with the third compound, the group or groups attached to the third moieties can be any group as long as the carbon atom attached to that group can be made to react with the amino group of the second compound. In particular, a strong nucleophile may be attached to the moiety. A strong nucleophile includes a methoxy group or a group that is a stronger nucleophile than a methoxy group. For example, chlorine and/or tetrazole may be attached to the moiety.

Where the third moiety is —COCOOCR$_3$, the group attached to the moiety may be identical to or a stronger nucleophile than the —OCR$_3$ group of the moiety. Thus, where each R in the moiety is a H, the group attached to the moiety may be a methoxy group or a group that is a stronger nucleophile than a methoxy group. Therefore, where the —OCR$_3$ group of the moiety is a weaker nucleophile than a methoxy group, the group attached to the moiety may be a weaker nucleophile than methoxy as long as it identical to or a stronger nucleophile than the —OCR$_3$ group in the moiety.

A compound containing at least two moieties, such as described in the above method, may be phosphitilated at a secondary or tertiary hydroxy group, particularly to add a phosphoramidite thereto. In particular, the hydroxy group at a secondary carbon may be phosphitilated. In embodiments where there are two hydroxy groups, the other hydroxy group may be protected by a protecting group so that only one hydroxy group is phosphitilated.

Phosphitilation at a secondary or tertiary hydroxy group provides for increased stability. However, phosphitilation at a secondary hydroxy group is particularly preferred because, with phosphitilation at a tertiary hydroxy group, steric hindrance problems may be introduced that counteract the increase in stability.

Phosphoramidite compounds with a phosphoramidite group at a secondary or tertiary carbon are preferable. Such an orientation increases the stability of the compound. In such compounds, degradation after storing at −20° C. may be prevented for 3–6 months, 1 year, 3 years or more. In addition, in embodiments, the phosphoramidite compounds may be in solid form. Solid phosphoramidite compounds generally show increased stability over phosphoramidite compounds in oil form.

Monomeric compounds that contain at least two hydroxy or protected hydroxy groups can undergo polymerization reactions that link the hydroxy groups. In an embodiment of the invention, phosphodiester linkages between the monomeric compounds may be formed by phosphitilation techniques known in the art.

In an embodiment of the invention, the first monomeric compound is a nucleoside or nucleotide. Known phosphitilation techniques may be used to form phosphodiester linkages between the monomeric compound and other organic moieties, which may or may not be a monomeric compound of the present invention, such that oligonucleotides, oligomers, polynucleotides or polymers can be formed.

In a preferred embodiment of the invention, oligonucleotides or oligomers are formed using a phosphoramidite method. In a further preferred embodiment of the invention, a double mode coupling protocol is used. A double mode coupling protocol means that there are two consecutive coupling steps, with only washing in between the coupling steps. In contrast, in the standard phosphoramidite method, capping occurs between each coupling reaction.

A number of terminus modifiers suitable for single and multiple functionalization of synthetic oligonucleotides and oligomers may also be synthesized according to methods of the present invention. The approach to synthesis of the modifiers is general and, thus, the practical issues, such as stability, solubility in CH$_3$CN, ease of handling and availability of a starting material, may also be addressed. The novel modifiers are heterobifunctional reagents, bearing, along with a phosphoramidite moiety, one or several precursor gorups, such as methoxyoxalamido groups. These groups serve as precursor groups for post-synthetic derivatization with an appropriate amine, preferably a primary amine. The synthesized modifiers may be successively used in the preparation of different oligonucleotides, such as 5'-modified oligonucleotides, and oligomers. The derivatization strategy allows manufacture of a vast number of functionalized oligonucleotides or oligomers from the same precursor oligonucleotide or oligomer.

Methoxyoxalamido and N-succinimido oligonucleotide and oligomer precursors can be synthesized from monomeric compounds by, for example, phosphoramidite solid-phase synthesis. Being treated with a nucleophile, these precursors, as well as the other precursors taught herein, may produce corresponding modified oligonucleotides or oligomers. A broad range of modified oligonucleotides or oligomers can be prepared from a single methoxyoxalamido or N-succinimido oligonucleotide or oligomer precursor.

If a precursor oligonucleotide or oligomer is treated with mixtures of different nucleophiles, modified oligonucleotide or oligomer combinatorial libraries can be created. These combinatorial libraries should be useful for many applications, for instance, for the search of powerful antisense/antigene drugs. This is particularly important because of the instability of natural oligonucleotides towards enzymes, such as nucleases. Backbone modified (phosphorothioates, methyl-phosphonates, etc.) modified oligonucleotides or oligomers and their combinatorial libraries can also be prepared by the described strategy.

Further modified polynucleotides or polymers can be obtained using methoxyoxalamido, N-succinimido and the other precursors taught herein.

Other uses of compounds of the present invention, such as for gene sequencing applications, are described in U.S. patent application Ser. No. 09/655,804, filed Sep. 5, 2000, the entire disclosure of which is hereby incorporated by reference.

Methoxyoxalamido and N-succinimido moieties may also be part of different diol systems. Being DMT-protected at one hydroxy and phosphitilated at another, such synthons can be used in, for example, phosphoramidite solid-phase synthesis to produce non-nucleoside oligomer precursors. These precursors will produce, upon treatment with an appropriate nucleophile, non-nucleoside phosphodiester oligomers or polymers, or, upon treatment with mixtures of different nucleophiles, non-nucleoside phosphodiester oligomer or polymer combinatorial libraries. Backbone modified (phosphorothioates, methylphosphonates, etc.) non-nucleoside phosphodiester oligomers and their combinatorial libraries can also be prepared by the described strategy. Any organic monomer unit can be used to form oligomer and polymers by the process taught herein as long as the monomer units are diols and contain or can be modified to contain a primary or secondary amine.

Precursor non-nucleoside and non-nucleotide compounds and synthesis of such compounds and oligomers are described in U.S. patent application Ser. No. 09/655,317, filed Sep. 5, 2000, the entire disclosure of which is hereby incorporated by reference.

EXAMPLES

Example 1

Terminus modifiers bearing two and four methoxyoxalamido groups may be prepared in a straightforward manner from trans-4-aminocyclohexanol and 5'-aminothymidine by iterative treatment with dimethyl oxalate and tris(2-aminoethyl)amine followed by standard phosphitilation of a hydroxyl group.

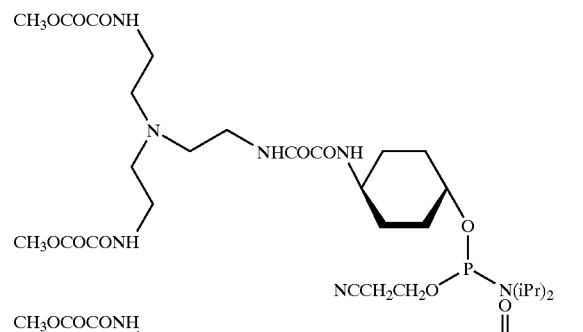

1

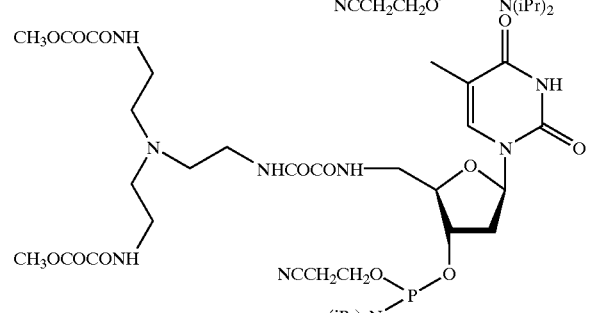

2

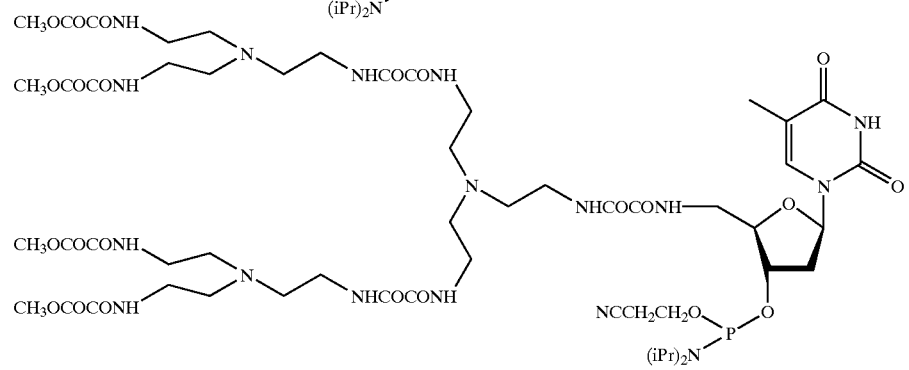

3

All three phosphoramidite containing compounds are stable compounds and soluble in $CH_3CN$— a common phosphoramidite solvent in automated oligonucleotide synthesis. Reactivity, however, differs considerably between compounds containing double and quadruple MOX terminators. Thus, at 1 μmol scale and with tetrazole as a catalyst, phosphoramidite containing compounds 1 and 2 effectively (>95%) couple in less than 3 minutes. While it takes about 15 minutes to ensure the same coupling yield for a bulkier phosphoramidite, such as compound 3 (FW=1386). The coupling time for compound 3 might be reduced to 10 min if more acidic 5-ethylthio-1H-tetrazole is used instead of tetrazole.

The methoxyoxalamido (MOX) moiety reacts very rapidly and virtually quantitatively with strong nucleophiles, such as primary aliphatic amines, which attack the highly electrophilic ester carbonyl carbon. Thus, upon introduction on an oligonucleotide molecule, a MOX moiety serves as a convenient site for further derivitization with a desirable additive, assuming that this additive contains a primary amino group. Efficiency and simplicity of this universal approach of oligonucleotide tethering has already been demonstrated. Terminus modifiers 1–3 were designed to introduce two and four MOX groups per phosphoramidite unit, and hence, allow multiple functionalization of a 5'-end. Their effectiveness was first established by tethering a model 10-mer oligothymidine (Table 1, entries 1–4).

TABLE 1

| Entry | Oligo-nucleotide | Modi-fying Units | Second Modifier | Yield, % (by CGE) | MW[a] (exper.) | MW (calc.) |
|---|---|---|---|---|---|---|
| 1 | (Tp)$_9$T | none | none | 82.4 | 2978.4 | 2979.9 |
| 2 | 1p(Tp)$_9$T | 1 | $NH_2(CH_2)_2NH_2$ | 70.3 | 3584.9 | 3586.5 |
| 3 | 2p(Tp)$_9$T | 2 | $NH_2(CH_2)_2NH_2$ | 69.7 | 3711.5 | 3711.6 |
| 4 | 3p(Tp)$_9$T | 3 | $NH_2(CH_2)_3NH_2$ | 74.6 | 4092.8 | 4092.2 |
| 5 | (Tp)$_4$(6p)$_5$T | 6 × 5 | $NH_2(CH_2)_2OH$ | 72.2 | 5278.4 | 5277.3 |
| 6 | 12 | 11 × 3 | none | 52.6 | 6625.9 | 6621.1 |
| 7 | 13 | 11 × 2, 1 | $NH_2(CH_2)_2Im$ | 54.1 | 9389.2 | 9385.2 |
| 8 | 14 | 6 × 2, 11, 3 | $NH_2(CH_2)_2Im$ | 47.7 | 10276 | 10280 |
| 9 | 15 | 11 × 2, 3 | $NH_2(CH_2)_2Im$ | 45.2 | 12793[b] | 12811 |
| 10 | 16 | 11, 6 × 4, 3 | $NH_2(CH_2)_2Im$ | 25.1 | c). | 15463 |

[a]ESI MS analysis;
[b]MALDI MS analysis;
c). Failed to acquire.

Modified uridine phosphoramidite 6 contains two MOX moieties attached through a 2'-position. It was synthesized from 5'-O-dimethoxytrityl-2'-N-succinimido-2'-deoxyuridine (compound 4 below) by opening the succinimidic cycle with tris(2-aminoethyl)amine, capping the two introduced amino groups with dimethyl oxalate and phosphitilating the 3'-hydroxyl (Scheme A).

Scheme A

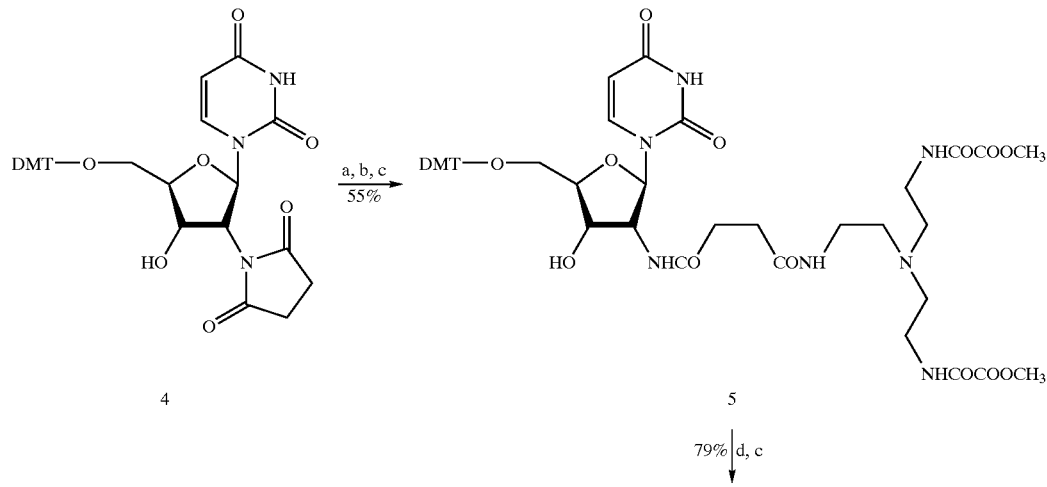

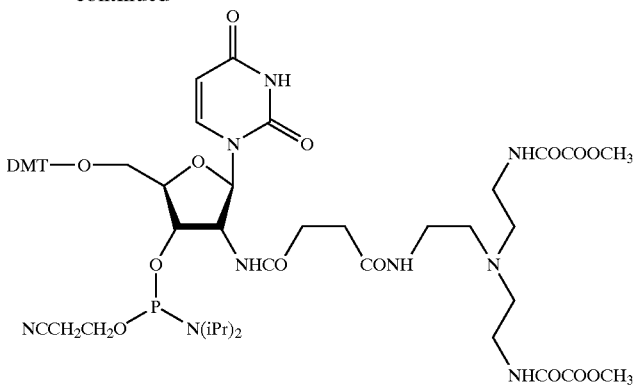

6 a: N(CH₂CH₂NH₂)₃
b: CH₃COCOOCH₃/Et₃N
c: Column chromatography
d: NCCH₂CH₂OP[N(iPr)₂]₂/Tetr The coupling time for phosphoramidite containing compound 6 was set to be 10 minutes to ensure a high yield incorporation (Table 1, entry 5).

Fork-like compound 11 (below) was synthesized in 4 steps from ethanolamine as it is outlined in Scheme B.

the MOX derivative was coupled to trans-4-aminocyclohexanol. Finally, the alcohol (compound 10) was phosphitilated into branching compound 11. Being a bulky molecule (FW=1106), phosphoramidite containing compound 11 needs an extended coupling time (up to 20

Scheme B

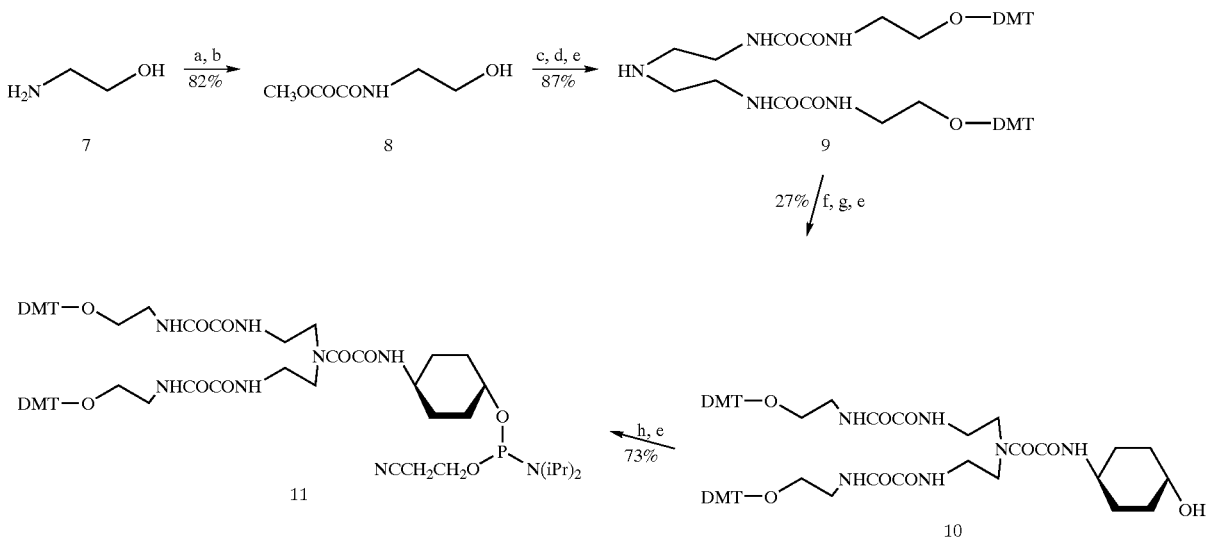

a: CH₃OCOCOOCH₃
b: Crystallization
c: DMT-Cl/Py
d: HN(CH₂CH₂NH₂)₂/Et₃N
e: Column chromatography
f: CH₃OCOCOTetr/Collidine
g: trans-4-Aminocyclohexanol hydrochloride/DBU
h: NCCH₂CH₂OP[N(iPr)₂]₂/Tetr The amino group of ethanolamine was transferred into a MOX group by treatment with dimethyl oxalate. The alcohol (compound 8) was first reacted with DMT-Cl to protect OH group and then with diethylenetriamine to produce compound 9. The secondary amino group of compound 9 was acylated with in situ prepared methoxyoxalo tetrazolide and minutes) and 5-ethylthio-1H-tetrazole as a catalyst to secure an excellent incorporation. A long distance between hydroxyl groups of the fork (for example, 17 atoms), however, allows efficient synthesis of highly branched structures. Thus, three generations of dendrimer 12 (below)

proceeding from 10-mer oligothymidine may be produced in approximately 53% overall yield (Table 1, entry 6).

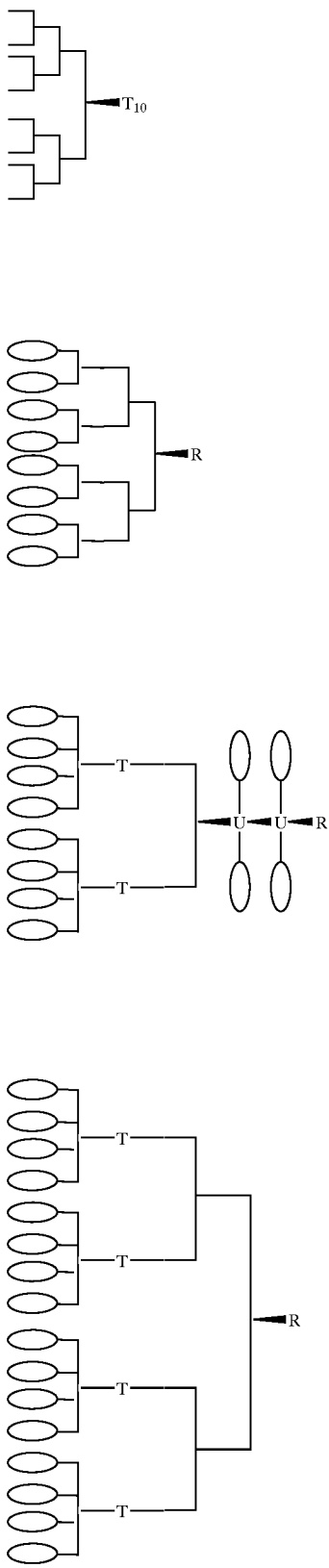
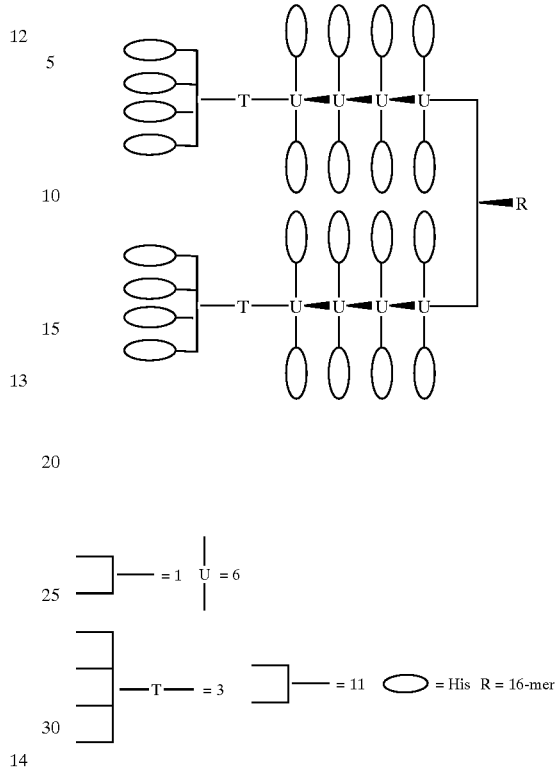

Having established conditions for incorporation of novel phosphoramidite groups, the synthesis of some oligonucleotides heavily functionalized with histamine residues is described. Such oligonucleotides, may be effective artificial ribonucleases. Deoxyoligonucleotide 5'-ATC GAA CAC AGG ACC T-3', that is a complement to the loop region of tRNA$^{Phe}$, was first synthesized by means of standard solid-phase phosphoramidite chemistry, except dC$^{Bz}$-phosphoramidite was substituted with dC$^{Ac}$-phosphoramidite. This substitution prevents N$^4$-side product formation during functionalization with histamine. The parent 16-mer (above) may then be further built up with modifying units, such as compounds 1–3 and 6, and/or branching unit 11, used in different combinations. The prepared multiple MOX precursors may then be functionalized with histamine (for example, by 2M solution in DMF, shaking for 2–6 hours at room temperature) and, finally, deprotected in a usual way. Four synthesized ribonuclease mimics having 8 (compound 13), 12 (compound 14), 16 (compound 15) and 24 (compound 16) histamine residues are schematically sketched above. The yields of the modified oligonucleotides are shown in Table 1, entries 7–10.

All synthesized ribonuclease mimics, indeed, showed high efficiency and specificity in cleaving target tRNA$^{Phe}$.

Scheme A

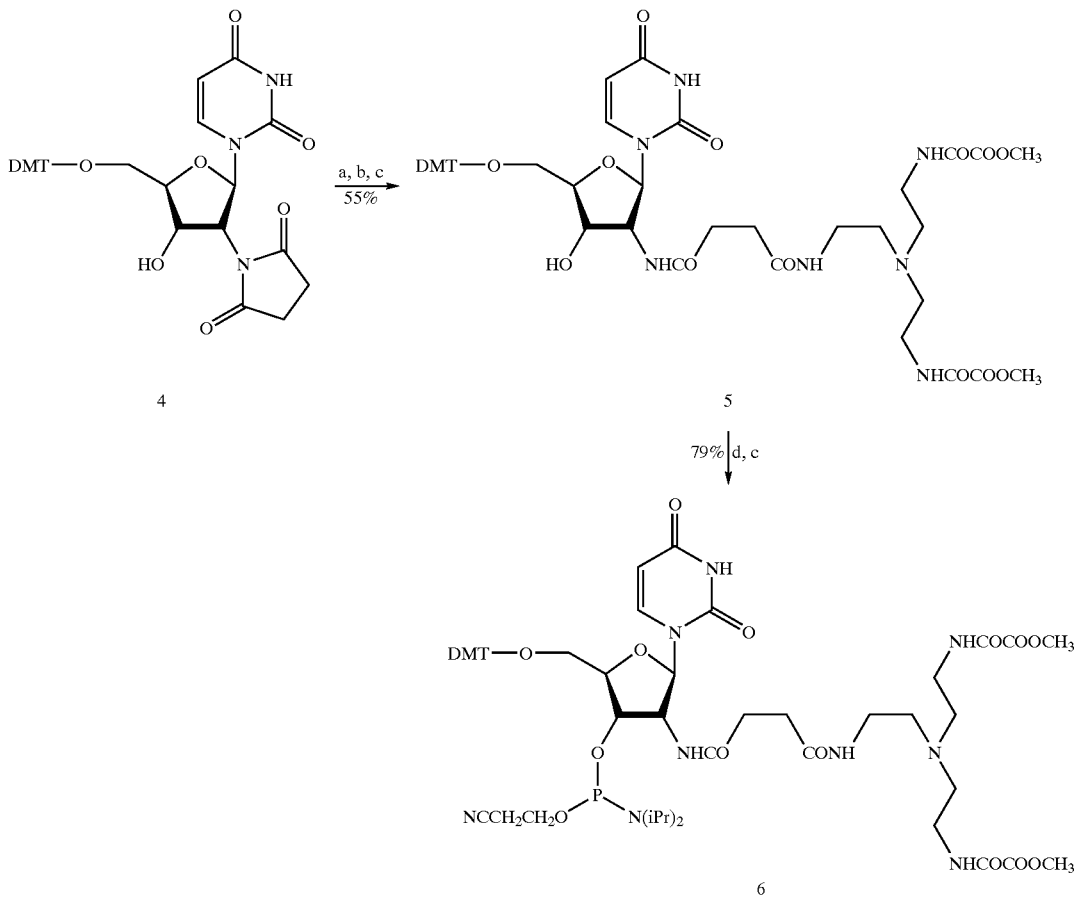

a: N(CH₂CH₂NH₂)₃
b: CH₃COCOOCH₃/Et₃N
c: Column chromatography
d: NCCH₂CH₂OP[N(iPr)₂]₂/Tetr Compound 4.) 5'-Dimethoxytrityl-2'-amino-2'deoxy-uridine (2.72 g, 5 mmole, prepared as in McGee, D. P. C.; Vaughn-Settle, A.; Vargeese, C.; Zhai, Y. J. Org. Chem. 1996, 61, 781–785) was diluted in acetonitrile (50 ml). To the solution collidine (3.48 ml, 20 mmole) and succinic anhydride (525 mg, 5.25 mmole) were consecutively added with stirring. The reaction mixture was stirred for 30 min and then concentrated to 25 ml. 2-(1H-Benzotriazol-1-yl)-1,1,3,3,-tetramrthyluronium, tetrafluoroborate, TBTU (2.41 g, 7.5 mmole, Chem-Impex International (Wood Dale, Ill.)) was added and the reaction mixture was left at room temperature overnight. CHCl₃ (300 ml) was added and the reaction mixture was extracted with saturated aqueous NaCl (300 ml). The organic phase was dried with Na₂SO₄ and concentrated. The crude product was column purified over silica gel (60 Å, 200 ml) using 0–10% gradient MeOH in CHCl₃ to give compound 4 (2.92 g, 4.65 mmole, 93%) as a white solid. ¹H-NMR (DMSO-d₆) δ11.34–11.43 (s, 1H, NH), 7.73–7.82 (d, 1H, H-6), 7.18–7.48 (m, 9H,DMT), 6.83–6.95 (m, 4H, DMT), 6.38–6.44 (d, 1H, H-1'), 5.56–5.62 (d, 1H, OH-3'), 5.48–5.56 (d, 1H, H-5), 4.63–4.75 (q, 1H, H-2'), 4.15–4.38 (m, 2H, H-3', 4'), 3.70–3.80 (m, 6H, OCH₃), 3.1–3.35 (m, 2H, CH₂-5'), 2.65–2.78 (s, 4H, 2CH₂); ESI MS m/z 627.9 (M+H⁺), 649.9 (M+Na⁺), 666.9 (M+K⁺).

Compound 5.) Compound 4 (3.13 g, 5 mmole) was taken into CH₂Cl₂ (30 ml). The solution was added to the solution of tris(2-aminoethyl)amine (5.25 ml, 35 mmole) in CH₂Cl₂ (30 ml). The reaction mixture was left at room temperature for 1.5 hrs. The reaction mixture was precipitated into ether (500 ml). The precipitate was filtered out and dissolved in MeOH (100 ml) containing triethyl amine (2.8 ml, 20 mmole). The solution was drop-wise added to the stirring solution of methyl oxalate (2.36 g, 20 mmole) in MeOH (50 ml) over 30 min. The reaction mixture was concentrated to 20 ml and ether (200 ml) was added. The precipitate was filtered out, dissolved in CHCl₃ (30 ml) and column purified over silica gel (60 Å, 200 ml) using 0–5% gradient MeOH in CHCl₃ to give compound 5 (2.41 g, 2.55 mmole, 51%) as a white solid. ¹H-NMR (DMSO-d₆) δ11.29–11.36 (s, 1H, NH), 8.65–8.2 (t, 2H, NHCOCO), 7.90–8.02 (d, 1H, NH-2'), 7.59–7.72(m, 2H, H-6+CONH), 7.18–7.48 (m, 9H,DMT), 6.83–6.95 (m, 4H, DMT), 5.83–5.92 (d, 1H, H-1'), 5.63–5.72 (d, 1H, OH-3'), 5.36–5.46 (d, 1H, H-5), 4.54–4.72 (q, 1H, H-2'), 4.09–4.20 (m, 2H, H-3'), 3.97–4.08 (m, 1H, H-4'), 3.70–3.83 (m, 6H, OCH₃), 3.00–3.35 (m, 10H, 4CH₂+ CH₂-5'), 2.23–2.70 (m, 10H, 5CH₂); ESI MS m/z 946.3 (M+H⁺), 968.3 (M+Na⁺).

Phosphoramidite 6 (extending nucleosidic 2MOX monomer). To alcohol 5 (1.89 g, 2 mmole) and tetrazole (182 mg, 2.6 mmole) CH₂Cl₂ (50 ml) and 2-cyanoethyl N,N,N',N'-tetraisopropylphosphoramidite (2.23 ml, 7.0 mmole) were added. The reaction mixture was stirred for 4 hrs. CH$_2$Cl$_2$ (50 ml) was added and the solution was extracted with saturated aqueous NaHCO$_3$ (100 ml). The organic phase was dried (Na$_2$SO$_4$) concentrated to dryness, taken into CH$_2$Cl$_2$ (20 ml) and precipitated into hexane:ether (3:4, 350 ml). The crude product was purified by flash chromatography over silica gel (60 Å, 50 ml) using 5–40% gradient of pyridine in ethylacetate. Fractions containing the product were combined and concentrated to dryness. The oily residue was dissolved in CH$_2$Cl$_2$ (20 ml) and precipitated in ether (200 ml). The precipitate was dried to give 6 as a white solid (1.81 g, 1.58 mmole, 79%). $^{31}$P-NMR (CDCl$_3$) δ145.8; 144.9; ESI MS m/z 1145.9 (M+H$^+$).

Oligomerization and Derivatization: (Tp)$_4$(U$^{2MOX-EA}$p)$_5$T.

Compound 6 (Scheme A) was used for the synthesis of mixed 10-mer containing 5 thymidines and 5 modified uridine blocks each bearing 2 MOX groups. Synthesis was performed on a ABI 394 DNA synthesizer at 1 µmole scale using the manufacture's suggested protocol except coupling time for compound 6 was set to be 10 min. T-amidite, T-CPG column and all ancillary DNA synthesis reagents were purchased from Glen Research (Sterling, Va.). Compound 6 was used as a 0.1 M solution in acetonitrile. Stepwise yields (trityl absorbency assay) were 97–100%. After the solid phase synthesis the oligomer-derivatized CPG was treated with ethanolamine (EA, 50 µl) for 24 hr at room temperature. The reaction mixture was then diluted with water to 500 µl and desalted on Sephadex G-25 NAP-10 column (Pharmacia, Uppsala, Sweden). The crude 10-mer was analyzed by capillary gel electrophoresis (CGE). According to CGE the yield is 72%. ESI MS spectra shows peaks corresponding to molecular weight 5278 D that is in accordance with calculated MW of 5277 D.

Example 3

It is known that an active center of ribonuclease A, an enzyme that cleaves RNA, contains 2 imidazole residues which are involved in catalytic cleavage. Many attempts were made to mimic ribonuclease A by introducing an imidazole moiety onto oligonucleotides. Oligonucleotides bearing only one imidazole moiety are not capable of cleaving their target RNA. Using MOX modifiers bearing 2 and 4 reactive groups, the present invention provides oligonucleotides containing 2 and 4 imidazole moieties, for example on the 5'-end. RNA cleaving experiments showed that an oligonucleotide with 2 imidazoles is an effective ribonuclease mimic, and an oligonucleotide with 4 imidazoles is substantially more effective than the one bearing 2 imidazoles (FIG. 1).

Better activity for 4 imidazole residues can be attributed to a higher density of functional groups and, thus, a higher probability that at least 2 of them will be spaced in a way allowing cooperation of action or, in other words, catalytic mode of action.

Synthesis of Oligonucleotides

The core deoxyoligonucleotide d(ATC GAA CAC AGG ACC T), which is complementary to the loop region of tRNA$^{Phe}$, was synthesized on a ABI 394 DNA synthesizer at 1 µmole scale using the manufacture's protocols. dC$^{Ac}$-amidite was used instead of dC$^{Bz}$-amidite. To produce ribonuclease mimics, the core deoxyoligonucleotide was built up with a single MOX modified compound, a double MOX modified compound (compound 2, Example 1) and quadruple MOX modified compound (compound 3, Example 1). The prepared MOX precursors were then functionalized with histamine (2 M solution in DMF, 50 µl, 1 h, room temperature). Ethanolamine (EA, 50 µl) was added and the reaction mixtures were left for 24 hr at room temperature. The reaction mixtures were then diluted with water to 500 µl and desalted on Sephadex G-25 NAP-10 column (Pharmacia, Uppsala, Sweden). For purification, modified oligonucleotides were loaded on polyacrylamide gel and run for 3 hrs at 400 V. Purified oligonucleotides were prepared by cutting out the corresponding bands, extracting them with 0.25 M triethylamino bicorbonate (TEAB) for 3–5 hrs at room temperature and desalting the oligonucleotide solutions on Sephadex G-25 (NAP-10 columns, Pharmacia). Structure of the 5'-end of modified oligonucleotides bearing 2 (R2) and 4 (R4) imidazole residues is shown below.

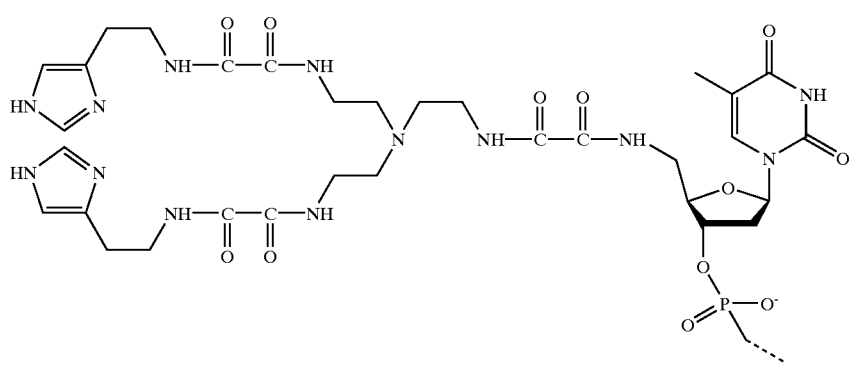

R2

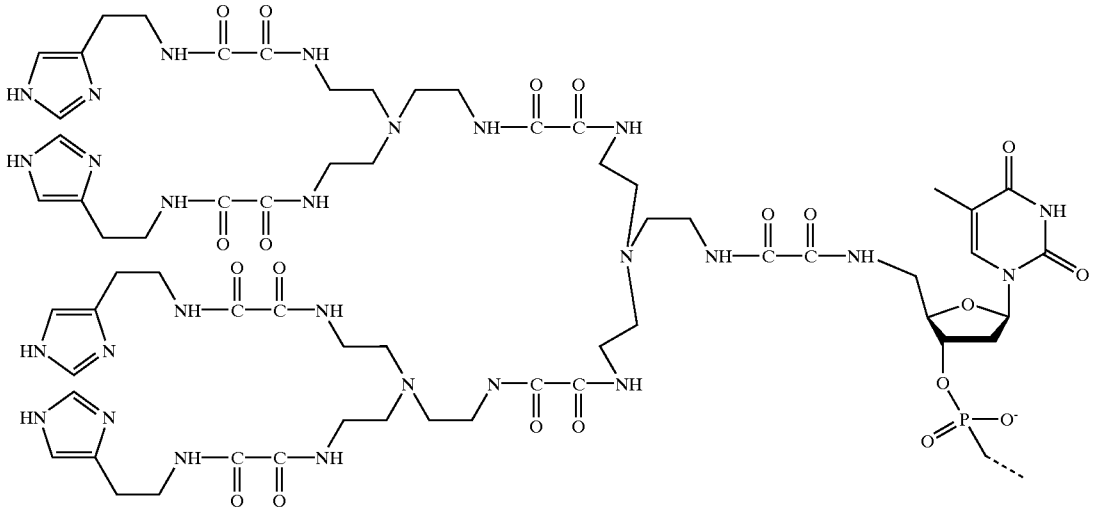

R4

3' End Labeling of Yeast tRNA$^{Phe}$

3'-[$^{32}$P]-tRNA$^{Phe}$ was obtained according to published protocols. 15 μl reaction mixture contained 50 mM HEPES-KOH pH 7.5; 10 mM MgCl$_2$; 10% DMSO; 0.1 mM ATP; 2 mM DTE; 100 μg/ml BSA; 160 pmol of tRNA; 200 μCi [$^{32}$p]-pCp and 20 u T4 RNA ligase. The reaction was performed overnight at 4° C. Labeled tRNA was purified by electrophoresis in 12% denaturing PAAG, RNA was eluted from the gel by 0.5 M ammonium acetate containing 1.0 mM EDTA and 0.1% SDS and ethanol precipitated. 3'-end labeled tRNA was dissolved in water and stored at −20° C. Specific activity of the obtained [$^{32}$P]-tRNA$^{Phe}$ was $5 \times 10^5$ cpm/pmole.

Cleavage of tRNA$^{Phe}$ with Oligonucleotide R2 and R4 (FIG. 4)

Reaction mixture (10 μl) contained 50 imidazole buffer, pH 7.0, 200 mM KCl, 1 mM EDTA, 100 μg/ml total tRNA from *Escherichia coli* as carrier, $5 \times 10^{-7}$ M 3'-[$^{32}$P]-tRNA$^{Phe}$ and oligonucleotide R2 or R4 at concentrations ranged from $5 \times 10^{-7}$ to $5 \times 10^{-4}$. Reactions were carried out at 37° C. and quenched by precipitation of tRNA and tRNA fragments with 150 μl of 2% lithium perchlorate solution in acetone. RNA was collected by centrifugation and dissolved in loading buffer (6 M urea, 0.025% bromophenol blue, 0.025% xylene cyanol). tRNA cleavage products were analyzed by electrophoresis in 12% denaturing PAAG. To identify cleavage sites imidazole ladder and partial RNase T1 digest of tRNA were run in parallel. To obtain quantitative data, gels were dried, radioactive bands were cut out of the gel and their radioactivity was determined by Cherenkov's counting. Total extent of tRNA cleavage was determined as ratio of radioactivity measured in each tRNA fragment to total radioactivity applied to the gel.

Cleavage reaction was performed at 37° C. in 50 mM imidazole buffer, pH 7.0, containing 200 mM KCl, 1 mM EDTA, 100 μg/ml total yeast tRNA as carrier, $5 \times 10^{-7}$ M 3'-[$^{32}$P]-tRNA$^{Phe}$. Conjugates concentrations were $1 \times 10^{-5}$ M.

As seen in FIG. 1, the modified oligonucleotide bearing 4 imidazole residues cleaves the target RNA in 1 hr while for the oligonucleotide with 2 imidazoles it takes more than 5 hrs to cleave the same target.

Example 4

The yields for phosphoramidite coupling are usually in the range 95–99%. At 95% coupling yield the overall yield of 4 couplings will be 0.95×0.95×0.95×0.95=0.81 (81%). Thus, if a monomer bearing 4 functional groups (for example, MOX) is used instead of a monomer with only 1 such a group there will be approximately a 14% (95−81=14) improvement in the overall yield in the synthesis of an oligonucleotide bearing 4 functional groups. The results of such a calculation are based on the assumption that coupling of both monomers are equally high. The transformation of MOX groups into final functions in both cases should proceed with equal yields if the same transformation conditions are used.

Example 5

Synthesis of Oligonucleotides Having Different Electrophoretic Mobility

T7 primer, d(GTA ATA CGA CTC ACT ATA GGG), was synthesized on a ABI 394 DNA synthesizer at 1 μmole scale using the manufacture's protocols. dC$^{Ac}$-amidite was used instead of dC$^{Bz}$-amidite. The core deoxyoligonucleotide was built up with a single MOX modifier compound and a double MOX (compound 2, Example 1) modified compound. The prepared MOX precursors were then functionalized with dansyl cadaverine (DC, 0.3 M solution in DMF, 50 μl, 1 h, 70° C.). Ethanolamine (EA, 50 μl) was added and the reaction mixtures were incubated at 70° C. for another 20 min. The reaction mixtures were then diluted with water to 500 μl and desalted on Sephadex G-25 NAP-10 column (Pharmacia, Uppsala, Sweden). For purification, modified oligonucleotides were loaded on polyacrylamide gel and run for 3 hrs at 400 V. Purified oligonucleotides were prepared by cutting out the corresponding bands, extracting them with 0.25M triethylamino bicorbonate (TEAB) for 3–5 hrs at room temperature, and desalting the oligonucleotide solutions on Sephadex G-25 (NAP-10 columns, Pharmacia).

Structure of the modified oligonucleotides bearing 1 (DC1mATT710) and 2 (DC2m$_2$ATT710) DC residues is shown below. The oligonucleotide, DC1mATT710, bearing 1 DC residue has slower mobility compared to underivatized T7 primer. DC2m$_2$ATT710 bearing 2 DC residues has the slowest mobility.

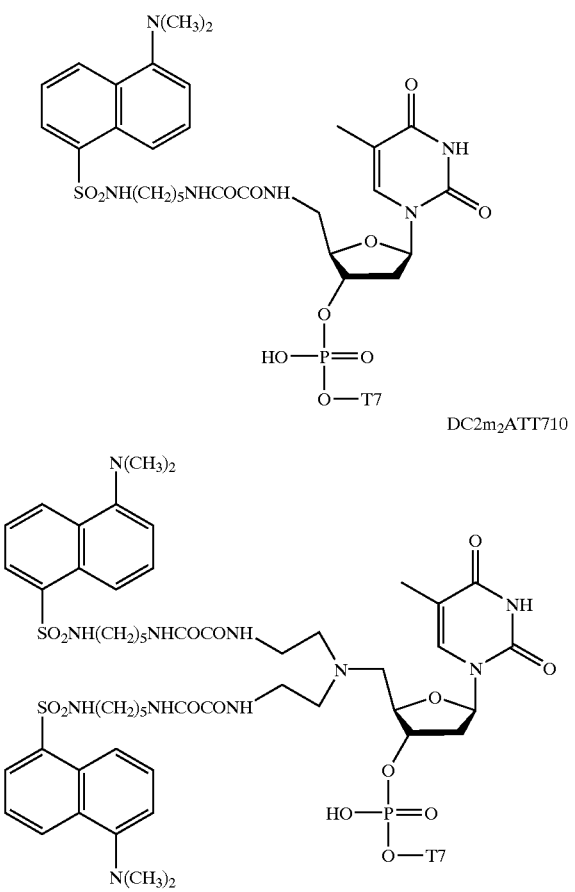

DC1mATT710

DC2m2ATT710

Example 6

Nonucleosidic Extending MOX Modifier with 2 MOX Groups

Compound 6 (di-MOX-di-alcohol, Scheme C, below). Dimethyl oxalate (9.21 g, 78 mmole) was taken into MeOH (30 ml). To this solution the solution of amine 1 in MeOH (60 ml) and triethylamine (14 ml) was dropwise added over 30 min. The reaction mixture was concentrated to 30 ml. Ether (150 ml) and hexane (100 ml) were added and the formed emulsion was left for separation. The supernatant was removed and the oily residue was diluted in MeOH (60 ml). The solution was portion-wise added to tris(2-aminoethyl)amine (22 ml, 150 mmole) with extensive stirring. Ether (300 ml) was added and the formed emulsion was left for separation. The supernatant was removed, the oily residue was taken into MeOH (30 ml) and precipitated into ether (300 ml) for the second time. The oily residue was diluted in MeOH (50 ml) and the solution was drop-wise added to the solution of dimethyl oxalate (21.3 g, 180 mmole) in MeOH (30 ml) and triethylamine (17 ml). The reaction mixture was concentrated to 40 ml and precipitated into ether (400 ml). The crude product was column purified over silica gel (60 Å, 600 ml) using 5–15% gradient MeOH in $CHCl_3$ to give 6 (25 g, 54 mmole, 90%) as a colorless glass. $^1$H-NMR (DMSO-$d_6$) $\delta$8.68–8.80 (t, 2H, NHCOCO), 8.55–8.68 (t, 1H, NHCOCO), 8.35–8.42 (t, 1H,COCONH), 4.86–4.92 (d, 1H, OH), 4.58–4.68 (t, 1H, OH), 3.73–3.82 (s+m, 7H, COCOOCH$_3$+CH), 3.02–3.64 (m, 10H, 5CH$_2$), 2.50–2.68 (t, 6H, 3CH$_2$); ESI MS m/z 463.9 (M+H$^+$), 485.9 (M+Na$^+$), 501.9 (M+K$^+$).

Scheme C

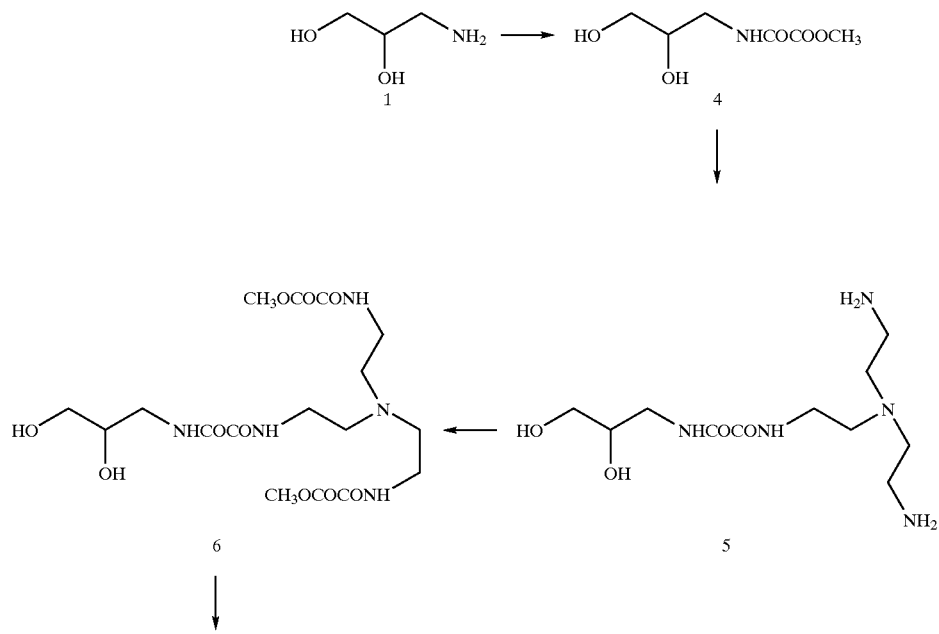

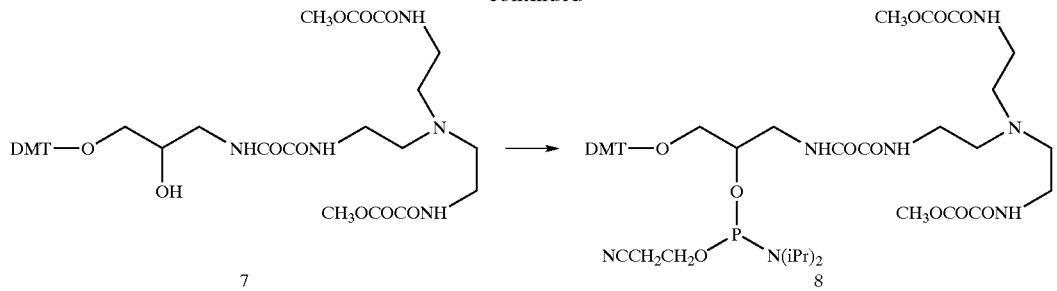

Compound 7 (Scheme C). Diol 6 (9.26 g, 20 mmole) was co-evaporated with pyridine and diluted in anhydrous pyridine (50 ml). DMTCl (8.47 g, 25 mmole) was added and the reaction mixture was left overnight. CHCl₃ (300 ml) was addded and the solution was extracted with saturated aqueous NaHCO₃ (300 ml). The organic phase was dried (Na₂SO₄) concentrated to dryness, taken into CHCl₃ (50 ml) and chromatograghed over silica gel (60 Å, 900 ml) using 0–5% gradient of MeOH in CHCl₃ to give 7 (8.57 g, 11.2 mmole, 56%) as a white solid. $^1$H-NMR (DMSO-d$_6$) δ8.70–8.80 (t, 2H, NHCOCO), 8.58–8.68 (t, 1H, NHCOCO), 8.26–8.38 (t, 1H,COCONH), 7.18–7.45 (m, 9H, DMT), 6.82–6.95 (d, 4H, DMT), 5.08–5.13 (d, 1H, OH), 3.70–3.86 (d, 13H, COCOOCH₃+OCH₃+CH), 3.09–3.45 (m, 8H, 4CH₂), 2.80–3.04 (m, 2H, CH₂), 2.50–2.68 (m, 6H, 3CH₂); ESI MS m/z 766.3 (M+H$^+$), 788.3 (M+Na$^+$).

Compound 8 (Scheme C). To alcohol 7 (2.3 g, 3 mmole) and tetrazole (190 mg, 2.71 mmol) CH₂Cl₂ (40 ml) and 2-cyanoethyl N,N,N',N'-tetraisopropylphosphoramidite (1.43 ml, 4.5 mmol) were added. The reaction mixture was stirred for 3 hrs. CHCl₃ (200 ml) was addded and the solution was extracted with saturated aqueous NaHCO₃ (200 ml). The organic phase was dried (Na₂SO₄) concentrated to dryness, taken into CH₂Cl₂ (20 ml) and precipitated into hexane (200 ml). The crude product was purified by flash chromatography (2% triethylamine in ethylacetate) to give 8 as a white solid (1.63 g, 1.69 mmol, 56%). $^{31}$P-NMR (CDCl₃) δ148.7; 148.8; ESI MS m/z 965.9 (M+H$^+$), 1067 (M+Et₃NH$^+$).

Oligomerization and Derivatization: (2MOX$^{EA}$p)$_{10}$(Tp)$_4$T.

Compound 8 was used for the synthesis of mixed 15-mer containing 5 thymidines and 10 non-nucleosidic blocks each bearing 2 MOX groups. Synthesis was performed on an ABI 394 DNA synthesizer at 1 μmole scale using the manufacturer's suggested protocol. T-amidite, T-CPG column and all ancillary DNA synthesis reagents were purchased from Glen Research (Sterling, Va.). Compound 8 was used as a 0.1 M solution in acetonitrile. Stepwise yields (trityl absorbency assay) were 92.4–100%. After the solid phase synthesis the oligomer-derivatized CPG was treated with ethanolamine (EA, 50 μl) for 1 hr at room temperature. The reaction mixture was then diluted with water to 500 μl and desalted on Sephadex G-25 NAP-10 column (Pharmacia, Uppsala, Sweden). The crude 15-mer was analyzed by capillary gel electrophoresis. The profile shows two major peaks which are attributed to the desired 15-mer (all 10 MOX groups are derivatized with EA) and partly hydrolyzed one (1–3 MOX groups are hydrolyzed to carboxyl groups). ESI MS spectra shows peaks corresponding to molecular weigh 7295 D, in accordance with calculated MW of 7288 D.

Example 7

Non-nucleosidic Compound with 6 MOX Groups

Compound 1 (below). The solution of tris(2-aminoethyl) amine (150 μl, 1 mmole) in MeOH (1 ml) was drop-wise added to the solution of dimethyl oxalate (1.06 g, 9 mmole) in MeOH (1 ml) and triethylamine (560 μl) over 30 min. Ether (10 ml) was to incur the precipitation. The supernatant was removed, the residue was taken into MeOH (1 ml) and precipitated into ether (10 ml). The precipitate was dried to give 1 as a white solid (182 mg, 0.45 mmole, 45%). $^1$H-NMR (DMSO-d$_6$) δ8.62–8.78 (t, 3H, NHCOCO), 3.72–3.83 (s, 9H, COCOOCH₃), 3.10–3.29 (q, 6H, 3CH₂), 2.52–2.66 (t, 6H, 3CH₂); ESI MS m/z 404.9 (M+H$^+$), 426.8 (M+Na$^+$), R$_f$=0.72 (CH₃Cl:MeOH=9:1).

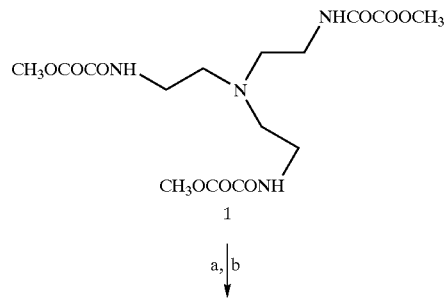

-continued

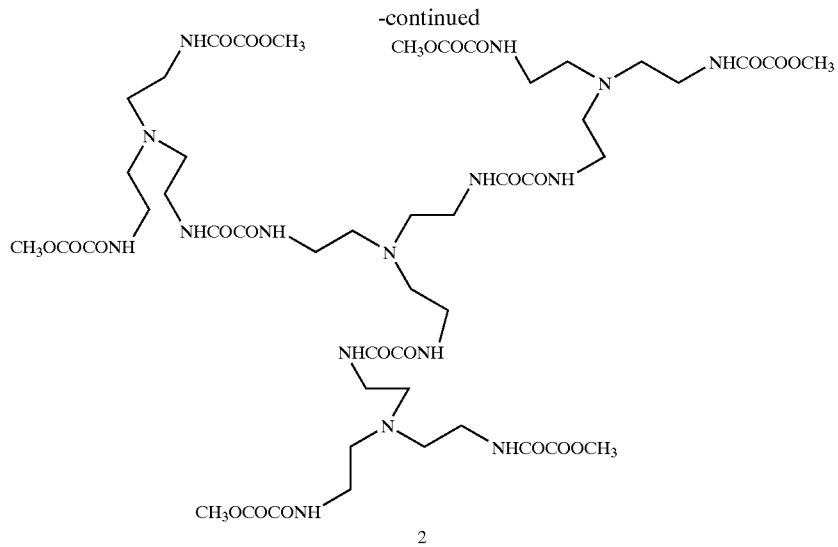

2

Compound 2 (6MOX). Compound 1 (40 mg, 0.1 mmole) was dissolved in MeOH (100 µl). The solution was added to tris(2-aminoethyl)amine (225 µl, 1.5 mmole) with stirring. The reaction mixture was left for 3 hrs at room temperature. Ether (8 ml) was added to incur precipitation. The supernatant was removed, the residue was dissolved in MeOH (1 ml). The precipitation was repeated 2 more times. The residue was dissolved in MeOH (1 ml) and the solution was drop-wise added to the solution of dimethyl oxalate (354 mg, 3 mmole) in MeOH (500 µl) and triethylamine (168 µl). The reaction mixture was left overnight. Ether (8 ml) was added to incur precipitation. The supernatant was removed, the residue was dissolved in MeOH (1 ml) and purified by preparative TLC (Silica gel 60, 2 mm thick) to give compound 2 as a white solid (13 mg, 0.01 mmole, 10%). ESI MS m/z 1263 (M+H$^+$), R$_f$=0.27 (CH$_3$Cl:MeOH=9:1).

What is claimed is:

1. A monomeric compound of formula (I) or of a salt of a compound of said formula (I):

$$A—X_n \quad (I)$$

wherein A represents an organic moiety selected from the group consisting of a substituted or unsubstituted alkane having from 3 to 100 carbon atoms, a substituted or unsubstituted cycloalkane having from 3 to 12 carbon atoms, and a substituted or unsubstituted heterocyclic compound having from 3 to 20 carbon atoms; n is at least 2; and each X is independently selected from the group consisting of: —NRCOCONu, —NHCOCR$_2$CR$_2$CONu, —NHCOCR=CRCONu, —NHCOSSCONu, —NRCOCOOCR$_3$,

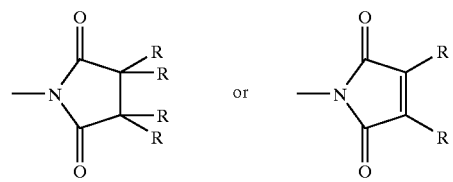 and

-continued

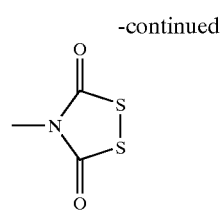

wherein Nu represents a nucleophile, each R independently represents H or a substituted or unsubstituted alkyl group, and where X is

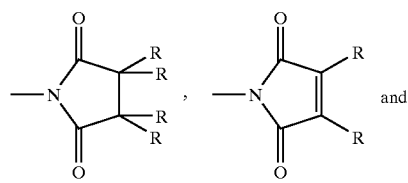 or then at least one R is a substituted or unsubstituted alkyl group.

2. The monomeric compound of claim 1, wherein said organic moiety is substituted with at least one substituent selected from the group consisting of a hydroxy group and a protected hydroxy group.

3. The monomeric compound of claim 1, wherein said organic moiety contains a single nucleoside or nucleotide.

4. The monomeric compound of claim 1, wherein said organic moiety is substituted with a phosphoramidite group.

5. The monomeric compound of claim 4, wherein said phosphoramidite group is attached to said organic moiety at a secondary carbon.

6. The monomeric compound of claim 1, wherein the nucleophile is selected from the group consisting of —O$^-$, an amino group, a primary amino group and a secondary amino group.

7. The monomeric compound of claim 1, wherein said organic moiety is substituted with at least two substituents selected from the group consisting of hydroxy groups and protected hydroxy groups.

8. The monomeric compound of claim 1, wherein said compound is joined through a phosphodiester linkage to a monomer, which may be the same or different, to form an oligomer, oligonucleotide, polymer or polynucleotide.

9. The monomeric compound of claim 8, wherein said phosphodiester linkage is at a secondary or tertiary carbon of said monomeric compound.

10. The monomeric compound of claim 1, wherein n is at least 3.

11. The monomeric compound of claim 1, wherein n is 4.

12. The monomeric compound of claim 1, wherein n is 6.

13. The monomeric compound of claim 1, wherein n is 8.

14. A method for forming a monomeric compound according to claim 1, comprising:

reacting a first compound containing at least two primary or secondary amino groups with at least a second and third compound, said second compound containing a second moiety and said third compound containing a third moiety, said second and third moiety each independently selected from the group consisting of: —COCOOCR$_3$, —COCR$_2$CR$_2$CO—, —COCR═CRCO— and —COSSCO— to form a fourth compound containing at least a fourth and fifth moiety, each selected from the group consisting of: —NRCOCOOCR$_3$,

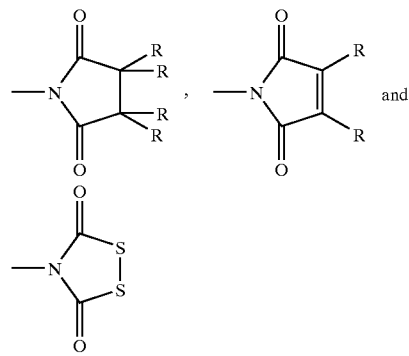

wherein each R independently represents H or a substituted or unsubstituted alkyl group.

15. A method for forming a compound of formula (I) or a salt of said compound of formula (I):

A—X$_n$     (I)

wherein A represents an organic moiety, n is at least 2, and each X is independently selected from the group consisting of: —NRCOCONu, —NHCOCR$_2$CR$_2$CONu, —NHCOCR═CRCONu, —NHCOSSCONu, —NRCOCOOCR$_3$,

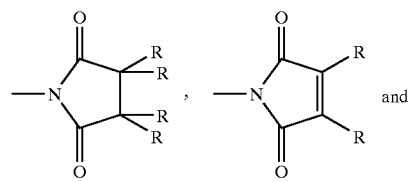

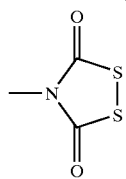

wherein each R independently represents H or a substituted or unsubstituted alkyl group, and Nu represents a nucleophile, said method comprising:

reacting, by nucleophilic addition, a first compound containing a first moiety selected from the group consisting of: —NRCOCOOCR$_3$,

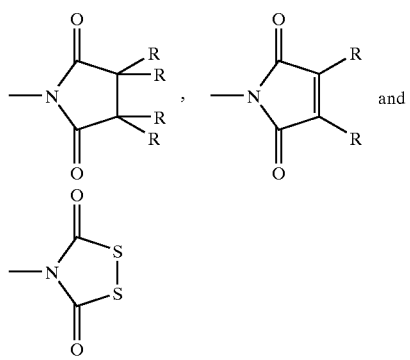

wherein each R independently represents H or a substituted or unsubstituted alkyl group, with a second compound (HNu) containing at least three primary or secondary amino groups to form a third compound containing a second moiety selected from the group consisting of: —NRCOCONu, —NHCOCR$_2$CR$_2$CONu, —NHCOCR═CRCONu, and —NHCOSSCONu, wherein each R independently represents H or a substituted or unsubstituted alkyl group, wherein one of said at least three primary or secondary amino groups of said second compound acts as a nucleophile in said nucleophilic addition, leaving at least two unreacted primary or secondary amino groups in said second moiety; and reacting said third compound with at least two compounds, which may be the same or different, each containing a third moiety independently selected from the group consisting of: —COCOOCR$_3$, —COCR$_2$CR$_2$CO—, —COCR═CRCO— and —COSSCO—, wherein each of said at least two compounds reacts with one of said at least two unreacted primary or secondary amino groups to form a compound containing at least two moieties independently selected from the group consisting of: —NRCOCOOCR$_3$,

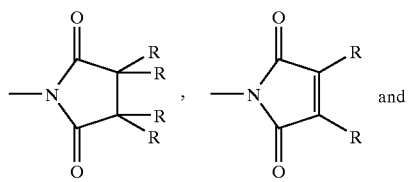

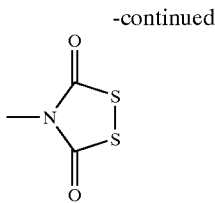

wherein each R independently represents H or a substituted or unsubstituted alkyl group.

16. The method of claim 15, further comprising reacting said compound containing at least two moieties with at least one monomer to form an oligomer or polymer.

17. The method of claim 15, further comprising phosphitilating said compound containing at least two moieties at a secondary or tertiary hydroxy group of said compound containing at least two moieties to form a phosphitilated compound containing said at least two moieties.

18. The method of claim 17, further comprising reacting said phosphitilated compound with at least one additional organic compound to form an oligomer or polymer that contains said at least two moieties.

19. The method according to claim 18, further comprising reacting a protonated nucleophile (HNu) with each of said at least two moieties of said oligomer or polymer to form a moieties selected from the group consisting of: —NRCOCONu, —NHCOCR$_2$CR$_2$CONu, —NHCOCR=CRCONu and —NHCOSSCONu.

20. The method according to claim 17, wherein the phosphitilated compound is reacted with at least one additional compound by phosphoramidite method.

21. The method according to claim 17, wherein said phosphitilated compound is reacted with at least one nucleoside or nucleotide to form said oligomer or polymer.

22. The method according to claim 17, wherein said third compound is phosphitilated at a secondary hydroxy group.

23. The method according to claim 15, wherein at least one of said at least three primary or secondary amino groups is a primary amino group.

24. A monomeric compound of formula (II) or of a salt of a compound of said formula (II):

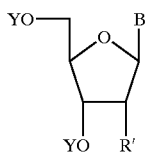

(II)

wherein each Y independently represents H, a group that protects a hydroxy group, a phosphorus containing group, a group reactive to link hydroxy groups, or a phosphodiester linkage to another compound, B is a nitrogenous base, and R' is an organic group that contains at least two functional groups independently selected from the group consisting of: —NRCOCONu, —NHCOCR$_2$CR$_2$CONu, —NHCOCR=CRCONu, —NHCOSSCONu, —NRCOCOOCR$_3$,

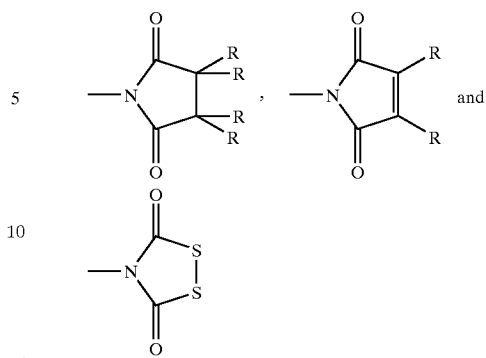

wherein each R independently represents H or a substituted or unsubstituted alkyl group, and Nu represents a nucleophile.

25. The monomeric compound of claim 24, wherein said phosphorus containing group is $(PO_3)_m^{-2}$.

26. The monomeric compound of claim 24, wherein the nucleophile is selected from the group consisting of —O$^-$, an amino group, a primary amino group and a secondary amino group.

27. The monomeric compound of claim 24, wherein n is at least 3.

28. The monomeric compound of claim 24, wherein n is 4.

29. The monomeric compound of claim 24, wherein n is 6.

30. The monomeric compound of claim 24, wherein n is 8.

31. The method of claim 15, wherein said first compound is a nucleoside or nucleotide that has been modified to contain said first moiety.

32. The method of claim 15, wherein said first compound is a compound of formula (II):

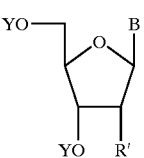

(II)

wherein each Y independently represents H or a group that protects a hydroxy group, B is a nitrogenous base, and R' is selected from the group consisting of: —NRCOCOOCR$_3$,

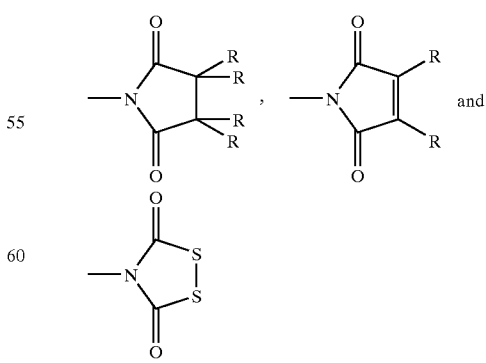

wherein each R independently represents H or a substituted or unsubstituted alkyl group.

33. The method of claim 15, wherein A represents an organic moiety containing a single nucleoside or nucleotide.

34. The method of claim 15, wherein A represents an organic moiety selected from the group consisting of a substituted or unsubstituted alkane having from 3 to 100 carbon atoms, a substituted or unsubstituted cycloalkane having from 3 to 12 carbon atoms, and a substituted or unsubstituted heterocyclic compound having from 3 to 20 carbon atoms.

35. The monomeric compound of claim 1, wherein X is independently selected from the group consisting of:
—NRCOCONu,    —NHCOCR$_2$CR$_2$CONu,
—NHCOCR=CRCONu,    —NHCOSSCONu,
—NRCOCOOCR$_3$, and

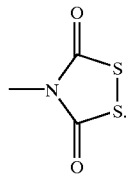

36. The monomeric compound of claim 24, wherein where at least one of said two functional group is

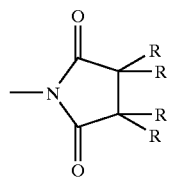 or 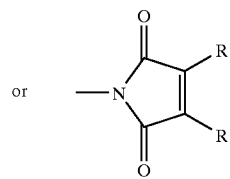

then at least one R in said functional group is a substituted or unsubstituted alkyl group.

37. The monomeric compound of claim 24, wherein X is independently selected from the group consisting of:
—NRCOCONu,    —NHCOCR$_2$CR$_2$CONu,
—NHCOCR=CRCONu,    —NHCOSSCONu,
—NRCOCOOCR$_3$, and

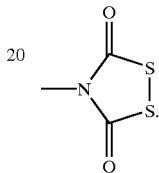

* * * * *